(12) United States Patent
Malla et al.

(10) Patent No.: US 8,273,097 B2
(45) Date of Patent: Sep. 25, 2012

(54) POWERED SURGICAL TISSUE CUTTING INSTRUMENT HAVING AN IRRIGATION SYSTEM

(75) Inventors: Aayush Malla, Fort Worth, TX (US); Charles Stanislaus, Jacksonville, FL (US); Joshua David Rubin, Jacksonville, FL (US); William C. Brunnett, Mission Viejo, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 180 days.

(21) Appl. No.: 12/771,699

(22) Filed: Apr. 30, 2010

(65) Prior Publication Data

US 2011/0270293 A1 Nov. 3, 2011

(51) Int. Cl.
*A61B 17/32* (2006.01)
(52) U.S. Cl. ........................... 606/167; 606/180
(58) Field of Classification Search .......... 606/167–180, 606/159, 115, 106, 107; 604/22, 46; 600/562–567
See application file for complete search history.

(56) References Cited

U.S. PATENT DOCUMENTS

| | | | |
|---|---|---|---|
| 5,195,541 A | | 3/1993 | Obenchain |
| 5,632,759 A | * | 5/1997 | Rexroth ........................ 606/180 |
| 5,810,863 A | * | 9/1998 | Wolf et al. .................... 606/185 |
| 6,068,641 A | * | 5/2000 | Varsseveld .................... 606/170 |
| 6,132,448 A | * | 10/2000 | Perez et al. ................... 606/180 |
| 6,312,438 B1 | | 11/2001 | Adams |
| 6,656,195 B2 | | 12/2003 | Peters et al. |
| 7,488,322 B2 | | 2/2009 | Brunnett et al. |
| 2002/0038129 A1 | | 3/2002 | Peters et al. |
| 2003/0163126 A1 | | 8/2003 | West |
| 2006/0241630 A1 | * | 10/2006 | Brunnett et al. ................ 606/80 |
| 2009/0270894 A1 | * | 10/2009 | Rubin et al. .................. 606/170 |

OTHER PUBLICATIONS

The International Search Report for Application No. PCT/US2011/032878, Jul. 22, 2011.

* cited by examiner

*Primary Examiner* — Elizabeth Houston
(74) *Attorney, Agent, or Firm* — Dicke, Billig & Czaja, PLLC

(57) ABSTRACT

A surgical tissue cutting instrument having an irrigation system comprises an elongate tubular outer member having a proximal end, a distal end and an opening at the distal end, an elongate inner member rotatably disposed within the outer member and having a proximal end, a distal end and a cutting element at the distal end exposed from the opening, a handpiece mounted to the proximal ends of the outer and inner members, and an irrigation system comprising an irrigation channel composed of a first irrigation passage within the handpiece and a second irrigation passage within the thickness of the annular wall of the outer member, and a sleeve having a rearward end disposed over a front end of the handpiece and a forward end disposed over the outer member adjacent an outlet opening of the second irrigation passage near the distal end of the outer member. The sleeve is disposed over the outer member with a snug fit while allowing communication through the outlet opening of the second irrigation passage, whereby the irrigation channel is enclosed and sealed between an inlet port of the first irrigation passage and the outlet opening of the second passage. The inlet port is connectible with a source of irrigation fluid for flow through the irrigation channel to be discharged from the outlet opening near the distal end of the outer member.

21 Claims, 4 Drawing Sheets

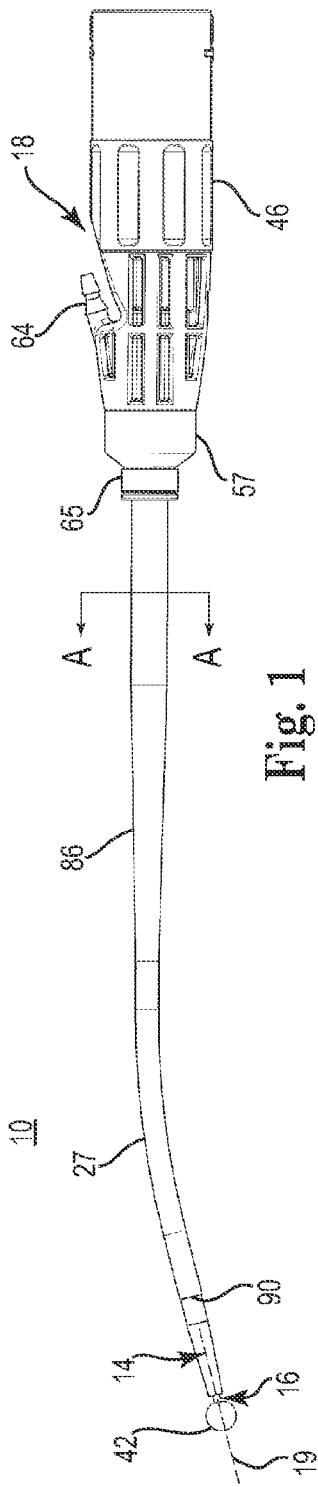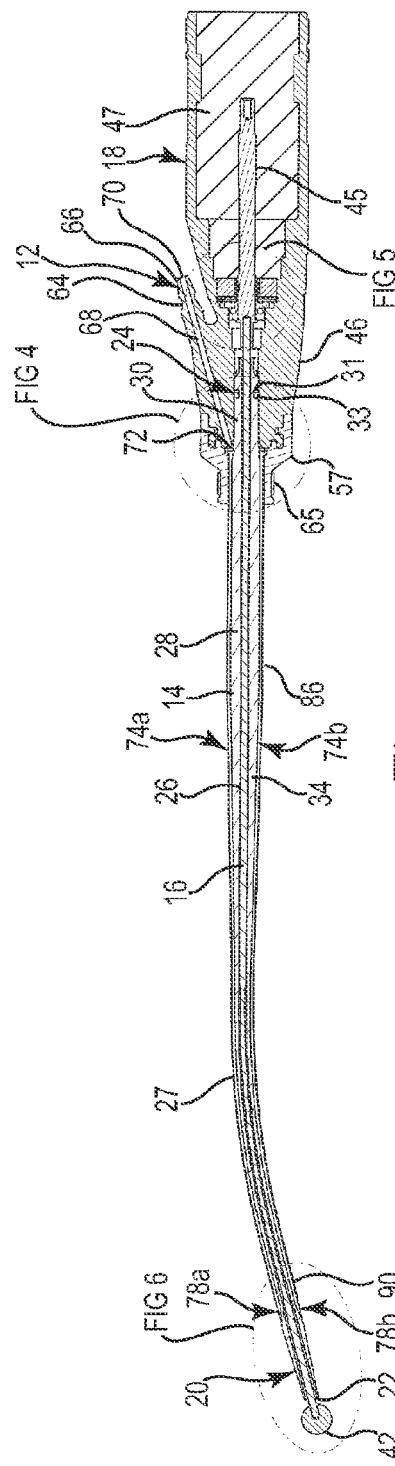

POWERED SURGICAL TISSUE CUTTING INSTRUMENT HAVING AN IRRIGATION SYSTEM

BACKGROUND

1. Field of the Invention

The present invention pertains to powered surgical tissue cutting instruments that have irrigation systems for supplying irrigation fluid to an internal operative site in a patient's body. More particularly, the present invention pertains to powered surgical tissue cutting instruments in which irrigation fluid is supplied through an irrigation channel that is external to the internal passage of a tubular outer member of the instrument.

2. Discussion of the Related Art

Powered surgical tissue cutting instruments in which an elongate inner member is rotated within the internal passage of an elongate tubular outer member are widely used in various surgical procedures for tissue removal or cutting. Such instruments are particularly well suited for use in endoscopic or minimally invasive surgical procedures carried out under visualization provided by an endoscope. In endoscopic or minimally invasive surgical procedures, the endoscope and other necessary instruments are introduced at an internal operative site in a patient's body via one or more natural or artificially created anatomical portals of relatively small size. Typically, the tubular outer member of the powered surgical tissue cutting instrument has a distal end with an opening, and the inner member thereof has a distal end with a cutting element exposed from the opening to contact anatomical tissue at the internal operative site. Normally, the outer member extends through a portal with the inner member within the outer member to position the cutting element at the internal operative site while proximal ends of the outer and inner members are maintained externally of the patient's body. The proximal ends of the outer and inner members are typically mounted to a powered surgical handpiece having a motor for rotating the inner member within the internal passage of the outer member so that the cutting element is rotated in order to effectuate removal or cutting of anatomical tissue at the internal operative site. It is generally desirable for the outer member to have an outer diameter as small in size as practicable so that the outer member can be introduced at the internal operative site through a portal that is minimized in size to reduce trauma to the patient.

Powered surgical tissue cutting instruments in which the inner member is rotated within the outer member may be referred to as rotary powered surgical tissue cutting instruments. Rotary powered surgical tissue cutting instruments may be designed as straight rotary powered tissue cutting instruments, wherein the outer member extends longitudinally from the handpiece to its distal end with a straight configuration and the inner member likewise has a longitudinally straight configuration of the outer member. In many surgical procedures, however, it is beneficial for rotary powered surgical tissue cutting instruments to be designed as curved or angled rotary powered surgical tissue cutting instruments to better access internal operative sites that are difficult to access with straight rotary powered surgical tissue cutting instruments. In such procedures, curved or angled rotary powered surgical tissue cutting instruments make it possible to properly introduce, position and manipulate the cutting element at the internal operative site quicker with improved visibility and with less trauma to the patient than straight rotary powered surgical tissue cutting instruments. Instruments that are known as curved or angled rotary powered surgical tissue cutting instruments are those in which the central longitudinal axis of the tubular outer member has at least one curve, angle or bend between the handpiece and the outer member distal end, and the inner member conforms to the curved, angled or bent configuration of the outer member while being rotated therein.

The cutting element at the distal end of the inner member in rotary powered surgical tissue cutting instruments can have various configurations depending on the type of anatomical tissue to be removed and/or depending on the type of cutting action to be performed with the instrument. In some rotary powered surgical tissue cutting instruments, the cutting element at the distal end of the inner member cooperates with a cutting element at the distal end of the outer member to cut anatomical tissue as a result of the inner member cutting element being rotated past the outer member cutting element. In other rotary powered surgical tissue cutting instruments, the cutting element at the distal end of the inner member includes a bur tip exposed from the opening in the distal end of the tubular outer member.

It is common for rotary powered surgical tissue cutting instruments to include irrigation systems for supplying irrigation fluid to the internal operative site. In curved rotary powered surgical tissue cutting instruments, the irrigation fluid is often supplied through a separate irrigation tube that is external to the tubular outer member and that extends alongside the external or outer diameter surface of the tubular outer member as represented by U.S. Pat. No. 6,312,438 B1 to Adams and U.S. Pat. No. 6,656,195 B2 to Peters et al. The irrigation tube is ordinarily attached to the outer member and/or to the powered handpiece. Irrigation fluid is supplied to the irrigation tube through a proximal inlet and is discharged from the irrigation tube through a distal outlet. In use, the irrigation tube extends through the anatomical portal alongside the outer member of the instrument, with the proximal inlet of the irrigation tube being disposed external of the patient's body for connection with a source of irrigation fluid, and the distal outlet of the irrigation tube being disposed near the distal end of the outer member for discharge of the irrigation fluid at the internal operative site.

The external irrigation tube adds bulk, mass, weight, size and volume to the rotary powered surgical tissue cutting instrument that may cause or contribute to surgeon fatigue while holding the instrument via the handpiece and/or may make it more difficult for the surgeon to properly manipulate the instrument via the handpiece. In order to accommodate the external cross-sectional size and configuration of the composite structure formed by the outer member and the external irrigation tube, the anatomical portal used for introduction of the instrument may need to be larger in size than would otherwise be required. The need for an anatomical portal of increased size is generally undesirable on account of the additional patient trauma associated therewith. Furthermore, the additional space taken up by the external irrigation tube may decrease or impair visibility of the internal operative site by the surgeon and/or reduce the amount of available free area or room within the patient's body available to the surgeon for maneuvering the instrument and/or the endoscope.

SUMMARY

The present invention relates to a surgical tissue cutting instrument comprising an elongate tubular outer member, an elongate inner member rotatably disposed within the outer member, a handpiece mounted to proximal ends of the outer and inner members, and an irrigation system comprising an irrigation channel composed of a first irrigation passage in the handpiece and a second irrigation passage in a thickness of the wall of the outer member. A sleeve includes a rearward end disposed over the outer member and a forward end adjacent an outlet opening of the second irrigation passage near a distal end of the outer member.

The outer member includes an open proximal end mounted to the handpiece, a distal end, an internal passage, and an opening at the distal end in communication with the internal passage. The outer member comprises a main body length section and a proximal length section joined to the main body length section. The main body length section has an external surface with an outer diameter, and a wall thickness between the external surface and the internal passage. The proximal length section has an external surface with an outer diameter smaller than the outer diameter of the main body length section to form an abutment surface between the external surface of the main body length section and the external surface of the proximal length section. The proximal length section is received in a chamber of the handpiece to mount the outer member in a fixed position on the handpiece. The inner member has a proximal end, a distal end, and a cutting element at the distal end. The inner member is rotatably disposed in the internal passage of the outer member with the cutting element exposed from the opening in the outer member to cut or remove anatomical tissue when the inner member is rotated. The proximal end of the inner member is mounted to the handpiece and is rotatably driven within the handpiece to rotate the inner member within the outer member. The main body length section of the outer member can have a curved, angled or bent configuration between the handpiece and the distal end of the outer member. In one embodiment, the cutting element on the inner member can be a bur.

The handpiece comprises a housing having a front end terminating distally at a front end surface, and a chamber within the housing having an access opening of the front end surface. The proximal length section of the outer member is received in the chamber with the abutment surface in contact or abutment with the front end surface of the housing. The proximal length section of the outer member may have a straight longitudinal configuration received coaxially in the chamber of the housing. The front end surface of the housing and the abutment surface of the outer member may be planar and perpendicular to a central longitudinal axis of the chamber. The housing further includes a neck and a locking formation. The chamber extends longitudinally through the locking formation and the neck. The chamber may be defined by an inner diameter surface of the housing having a diametric size to receive the proximal length section of the outer member with an interference or press-fit. The handpiece further comprises an irrigation extension extending from the front end of the housing to an end of the irrigation extension that is connectible with a source of irrigation fluid. A boot can be positioned over the locking formation.

The irrigation system comprises an irrigation channel composed of a first irrigation passage within the handpiece and a second irrigation passage within the wall thickness of the main body length section of the outer member, and a sleeve disposed over the main body length section of the outer member. A third irrigation passage may also be provided within the wall thickness of the main body length section. The first irrigation passage has an inlet port in the end of the irrigation extension and an exit opening on the front end surface of the housing. The first irrigation passage extends from the inlet port and through the irrigation extension and the neck to the exit opening. The first irrigation passage may extend through the housing and the exit opening may be disposed on the forward end surface The second irrigation passage comprises a groove in the external surface in the main body length section of the outer member having an entry opening on the abutment surface and an outlet opening at or near the distal end of the outer member. The third irrigation passage may be similarly constructed to the second irrigation passage. The groove has an open side along the external surface of the main body length section and is disposed within the wall thickness of the main body length section. The entry opening of the groove is aligned with the exit opening of the first irrigation passage when the abutment surface is in abutment with the front end surface of the housing. The first irrigation passage and the groove aligned therewith form the irrigation channel for the flow of irrigation fluid from the inlet port of the first irrigation passage to the outlet opening of the groove. The irrigation system further comprises a sleeve having a rearward end and a forward end disposed over the main body length section of the outer member adjacent the outlet opening of the groove. The sleeve is disposed on the main body length section with a snug fit while allowing communication through the outlet opening of the groove for the discharge of irrigation fluid from the irrigation channel, whereby the irrigation channel is enclosed and sealed between the inlet port of the first irrigation passage and the outlet opening of the second irrigation passage. The sleeve may be heat shrunk on the main body length section of the outer member to establish the snug fit.

Various objects, advantages and benefits realized with the present invention will become apparent from the following detailed description of a preferred embodiment taken in conjunction with the drawings.

BRIEF DESCRIPTION OF THE DRAWINGS

FIG. 1 is a side view of a powered surgical tissue cutting instrument having an irrigation system.

FIG. 2 is a side view of the powered surgical tissue cutting instrument in longitudinal cross-section and showing the irrigation system of the instrument.

DETAILED DESCRIPTION

Figure 3:
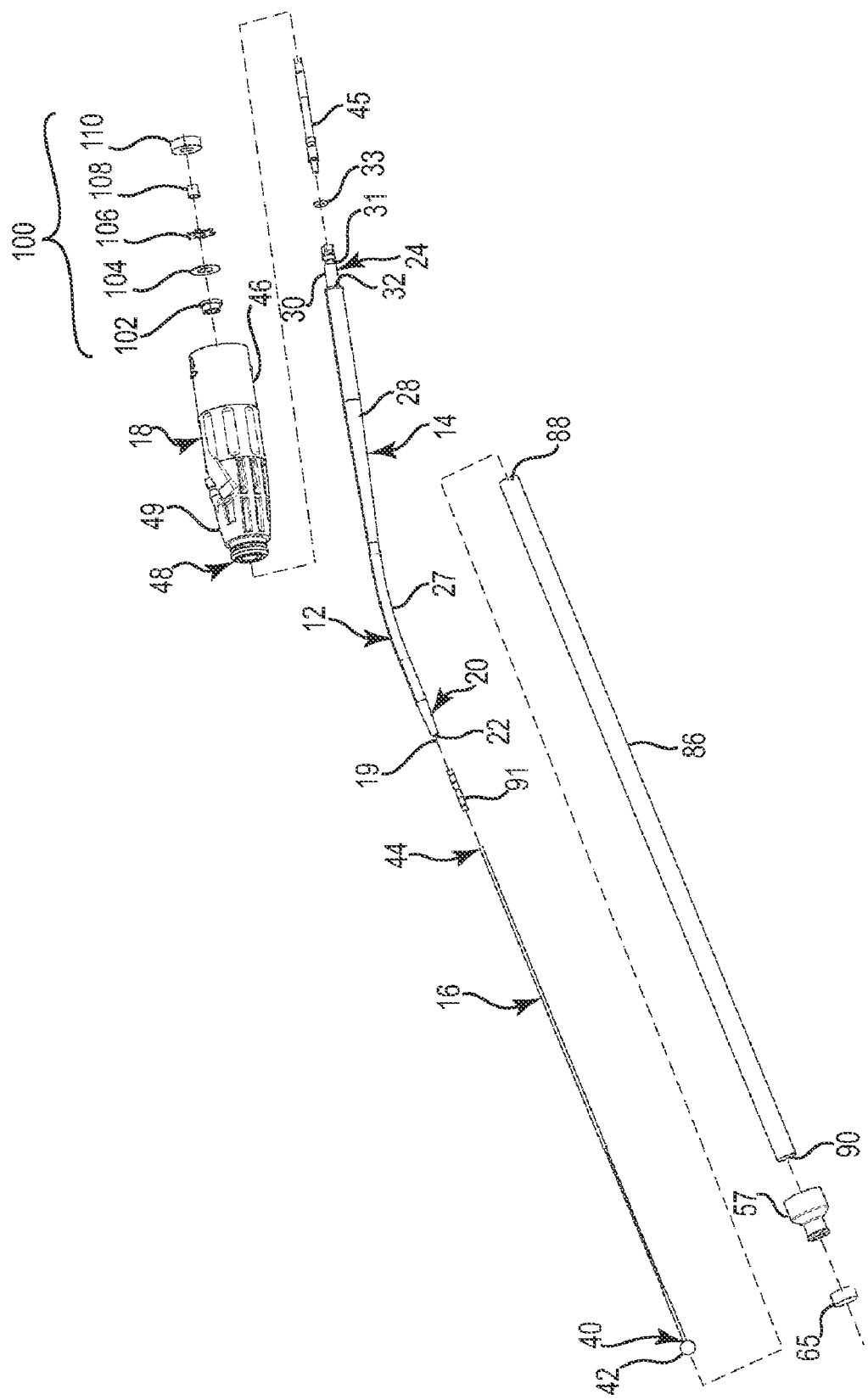
FIG. 3 is an exploded view of the powered surgical cutting instrument and showing the irrigation system of the instrument.

A powered surgical tissue cutting instrument 10 having an irrigation system 12 is illustrated in FIGS. 1-3. The powered surgical tissue cutting instrument 10 includes an elongate tubular outer member 14, an elongate inner member 16 movably disposed within the outer member, and a powered surgical handpiece 18 mounted to proximal ends of the outer and inner members. As explained further below, the inner member 16 is rotatable relative to and within the outer member 14 via a motor of the handpiece 18, and the instrument 10 can therefore be referred to as a rotary powered surgical tissue cutting instrument.

The tubular outer member 14 has a central longitudinal axis 19, a distal or forward end 20, a distal opening 22 at or near the distal end 20, an open proximal or rearward end 24 mounted to the handpiece 18, and an internal passage or lumen 26 that extends longitudinally within the outer member 14 in continuous communication with the distal opening 22 and the open proximal end 24. The instrument 10 is an example of a curved or angled rotary powered surgical tissue cutting instrument in which the outer member 14, and thus its central longitudinal axis 19, has at least one curve, angle or bend 27 between the handpiece 18 and the distal end 20 of the outer member. The outer member 14 thusly extends longitudinally from the handpiece 18 in the distal or forward direction with a curved, angled or bent configuration. The terms "curve"/"curved", "angle"/"angled", and "bend"/"bent" as used herein are intended to be encompassed within the definition of a "curved rotary powered surgical tissue cutting instrument." Although the irrigation system 12 is depicted herein as being implemented in a curved rotary powered surgical tissue cutting instrument, it should be appreciated that the irrigation system 12 can be implemented in a straight rotary powered surgical tissue cutting instrument in which the outer member 14, and thus its central longitudinal axis 19, extend longitudinally from the handpiece 18 to the distal end 20 with a continuously straight configuration.

Figure 4:
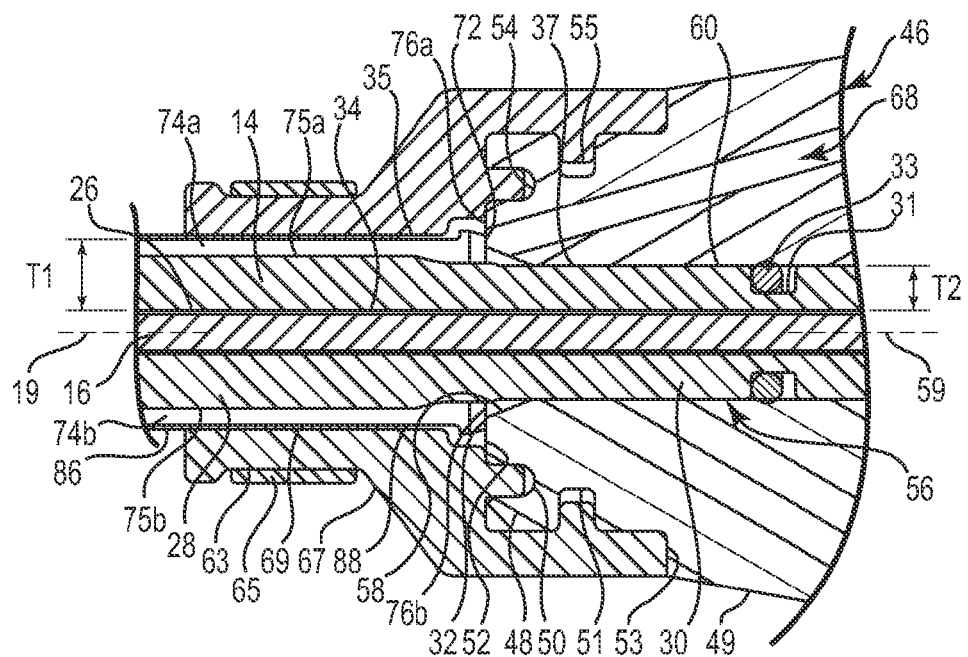
FIG. 4 is a close-up side view of the powered surgical cutting instrument in longitudinal cross-section showing connection of a handpiece with an outer tubular member.

The proximal end 24 of the outer member 14 is mounted or secured in the handpiece 18 such that the outer member 14 is maintained in or essentially in a stationary or fixed position on the handpiece 18. As illustrated in FIGS. 2-4, the outer member 14 comprises a tubular, cylindrical main body length section 28 and a tubular, cylindrical proximal length section 30 extending proximally from the main body length section 28. The main body length section 28 and the proximal length section 30 are coaxial with the central longitudinal axis 19. The proximal length section 30 of outer member 14 has an external surface with an outer or external diameter that is smaller in size compared to the main body length section 28 of the outer member 14. The main body length section 28 has an external surface with an outer or external diameter that is larger or greater in size than the outer or external diameter of the proximal length section 30 and forms an abutment surface 32 at its junction with the proximal length section 30. The proximal length section 30 extends proximally or rearwardly from the abutment surface 32 to terminate at the open proximal end 24 of the outer member 14. The proximal length section 30 has a longitudinally straight configuration, and therefore a section of the central longitudinal axis 19 along the proximal length section 30 is also longitudinally straight. The abutment surface 32 is annular, as it extends peripherally or circumferentially around the external surface of the proximal length section 30. The abutment surface 32 is planar, and the plane of the abutment surface is perpendicular to the straight section of the central longitudinal axis 19 along the proximal length section 30. As explained further below, the outer diameter of the proximal length section 30 is of a size to be received in the chamber of the handpiece 18 with a press-fit to retain or secure the outer member 14 to the handpiece 18 with the abutment surface 32 in abutment with a front end surface of the handpiece. In one embodiment, proximal length section 30 defines a recess 31 configured to receive a sealing member 33 (e.g., an o-ring) to provide a seal with the chamber of the handpiece 18. The outer member 14 is preferably made of steel suitable for surgical use.

The outer member 14 has an internal or inner diameter surface 34 defining the internal passage 26 coaxial with the central longitudinal axis 19. As seen in FIG. 4, the outer member has a first radial wall thickness T1 between an internal surface 34 and an external surface 35 of the main body length section 28, and has a second radial wall thickness T2 between the internal surface 34 and an external surface 37 of the proximal length section 30. The internal surface 34 defines an inner diameter of the outer member 14 that corresponds to the diametric size of the internal passage 26. The internal passage 26 is of a diametric size to rotatably receive the inner member 16 within the passage 26. The passage 26 may be of uniform diametric size between the distal opening 22 and the open proximal end 24 of the outer member 14. The radial wall thickness T1 of the main body length section 28 is greater than the radial wall thickness T2 of the proximal length section 30 due to the larger outer diameter of the main body length section 28 compared to the outer diameter of the proximal length section 30.

Figure 6:
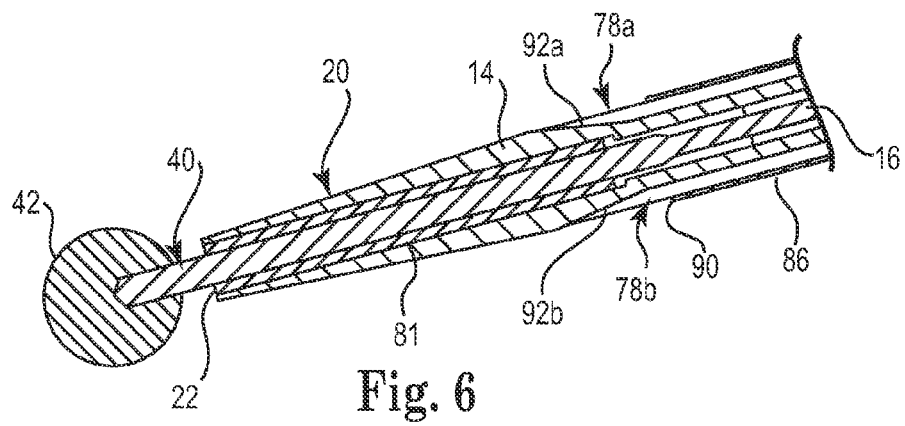
FIG. 6 is a close-up side view of the powered surgical cutting instrument in longitudinal cross-section showing a distal end thereof.

The inner member 16 is rotatably disposed within the internal passage 26 of the outer member 14 and has a distal or forward end 40 with a cutting element 42 exposed from the distal opening 22 in the outer member 14 and has a proximal or rearward end 44 coupled to a tang 45, for example by welding the rearward end 44 to the tang 45. The inner member 16 extends proximally from the open proximal end 24 of the outer member 14, and the proximal end 44 of the inner member 16 is coupled with the tang 45. In turn, the tang 45 is coupled to a motor 47 (schematically shown) to effectuate rotation of the inner member relative to the outer member. Due to the configuration of handpiece 18, the motor 47 can be inserted into a proximal end of the handpiece 18 so as to automatically lock the tang 45 (and thus cutting element 42) with respect to the motor in a simple, easy assembly process. To this end, instrument 10, in one embodiment, can be a single-use item that can be attachable to a reusable electric motor. In one embodiment, a bushing 91 can be disposed over distal end 40 of inner tubular member 16 to form a bearing between outer member 14 and inner member 16. FIG. 6 shows bushing 91 press fit into distal end 20 of outer member 14.

The inner member 16 further includes a flexible region (not shown) along a segment of its length disposed within the curve, angle or bend of the outer member 14 that allows the inner member 16 to rotate within the outer member 14 while conforming to the angled, curved or bent configuration of the outer member. The flexible region can be designed in various ways to transmit torque from the proximal end 44 of the inner member 16 to the cutting element 42 when rotation of the inner member is effectuated via the motor 47 of the handpiece 18.

Flexible regions for the inner members used in rotary surgical tissue cutting instruments to allow the inner member to conform to a curved, angled or bent configuration of the tubular outer member while being rotated therein are conventionally known in the field of rotary surgical tissue cutting instruments. Examples of flexible regions for the inner members of angled or curved rotary surgical tissue cutting instruments are taught in U.S. Pat. No. 6,656,195 B2 to Peters et al. U.S. Pat. No. 6,312,438 B1 to Adams and U.S. Pat. No. 7,488,322 B2 to Brunnett et al., the disclosures of which are incorporated herein by reference. The flexible region of the inner member 16 may be like those disclosed in the aforesaid patents or may be any other appropriate flexible region. Depending on the design of the flexible region and/or other factors, the inner member 16 may be tubular at least along the flexible region. However, the inner member 16 could be tubular or provided with an interior passage or lumen from an open proximal end of the inner member to an opening at or near the distal end of the inner member. The distal opening and the interior passage of the inner member may be used to aspirate fluid and tissue as conventionally known in the field of rotary surgical tissue cutting instruments. The inner member 16 is preferably made of steel suitable for surgical use.

The cutting element 42 at the distal end 40 of the inner member 16 is depicted as a bur that is situated and exposed beyond the distal opening 22 of the outer member 14. The instrument 10 may thusly be referred to as a curved rotary bur tissue cutting instrument. Although the irrigation system 12 is thusly depicted herein implemented in a curved rotary bur tissue cutting instrument, it should be appreciated that the irrigation system 12 can be implemented in rotary surgical tissue cutting instruments wherein the inner member cutting element 42 is different from a bur. Also, the irrigation system 12 can be implemented in rotary surgical tissue cutting instruments wherein the outer member 14 has a cutting element at or near its distal end, and the cutting element of the inner member cooperates with the cutting element of the outer member to cut anatomical tissue as the inner member cutting element is rotated past the outer member cutting element. In one embodiment, instrument 10 is configured for bone cutting.

The powered surgical handpiece 18 includes a housing 46, preferably having a configuration suitable for being grasped and held in the hand used to manipulate and maneuver the instrument. The housing 46 encloses the motor 47, which is typically an electric motor, used to rotatably drive the inner member 16 that is coupled to the motor in any suitable way. The handpiece 18 may be similar to the Stylus and Legend handpieces of Medtronic Surgical Technologies. With reference to FIG. 4, the housing 46 has a front end including a locking formation 48 and a neck 49 proximally joined to the locking formation 48. The locking formation 48 includes a first recessed locking portion 50, a second recessed locking portion 51, a front end surface 52 and a shoulder surface 53 joined to the external surface of the neck 49. Locking portions 50 and 51 are configured to receive corresponding tabs 54 and 55, respectively, of a boot or retainer 57. Boot 57 is generally flexible, allowing tab 55 to deflect during assembly so as to enter into locking portion 51. Moreover, a rearward end of the boot 57 is positioned against shoulder surface 53. In one embodiment, locking portions 50 and 51 are generally orthogonal to one another such that tabs 54 and 55 form seals against the locking portions 50 and 51, respectively, to prevent fluid from flowing outside of the boot 57 and housing 46. An inner diameter surface 61 of the boot 57 is sized to receive the outer member 14 and a recess 63 in the boot 57 receives a locking ring 65, configured to secure the boot 57 to the outer member 14. The external surface of neck 49 extends from the shoulder surface 53 in the proximal or rearward direction with an outward flare. Thus, the external cross-section of neck 49 increases in size in the proximal or rearward direction from the shoulder surface 53.

The housing 46 has a chamber 56 extending longitudinally therein in a rearward or proximal direction from an access opening 58 of the chamber disposed on or along the front end surface 52. The chamber 56 has a central longitudinal axis 59 and is defined by an inner diameter surface 60 of the housing 46. The chamber 56 and inner diameter surface 60 extend longitudinally from the access opening 58 in the proximal or rearward direction within and through the locking formation 48 and into the neck 49. The central longitudinal axis 59 of the chamber 56 is longitudinally straight, and the chamber 56 has a diametric size to receive the proximal length section 30 of the outer member 14 through the access opening 58 and into the chamber 56 with a press or interference fit to secure the outer member 14 in or essentially in a fixed or stationary position on the handpiece 18. In other words, the outer diameter of the proximal length section 30 is of a size to engage with the inner diameter surface 60 of the housing 46 to establish the press or interference fit, which also creates a seal between the external surface of the proximal length section 30 and the inner diameter surface 60 of the housing. Sealing member 33 provides an additional seal between proximal length section 30 and inner diameter surface 60. When the proximal length section 30 of the outer member 14 is retained or secured in the chamber 56 of the housing 46, the section of the central longitudinal axis 19 that extends along the proximal length section 30 is coaxial with the central longitudinal axis 59 of the chamber 56. The front end surface 52 of the housing 46 extends peripherally or circumferentially around the access opening 58 of the chamber 56, and the plane of the front end surface 52 is perpendicular to the central longitudinal axis 59 of the chamber 56 for surface-to-surface abutment or contact with the abutment surface 32 of the outer member 14 when the proximal length section 30 of the outer member is fully received in the chamber 56. When the proximal length section 30 is fully received in the chamber 56, the main body length section 28 extends distally from the handpiece 18. During use of the instrument 10 to cut or remove tissue in a surgical procedure, the main body length section 28 is introduced, distal end first, through a natural or artificially created anatomical portal to access an internal operative site in a patient's body while the handpiece 18 is maintained externally of the patient's body.

With reference to both FIGS. 2 and 4, a first irrigation passage 68 is disposed within the handpiece 18 and forms part of the irrigation system 12. The handpiece 18 includes an irrigation extension 64 joined to the front end of the housing 46. The irrigation extension 64 has a forward end joined to the neck 49 and the irrigation extension 64 extends lengthwise from the neck 49 toward the proximal or rearward direction to terminate at an inlet port 70 within a fitting 66 at a rearward end of the irrigation extension 64. The first irrigation passage 68 extends from the inlet port 70 in the fitting 66 to an exit opening or hole 72 on the front end surface 52 in fluid communication with access opening 58, which in one embodiment forms a beveled or chamfered surface. The irrigation passage 68 thusly extends from the inlet port 70 through the irrigation extension 64 and the neck 49 to the exit opening 72. The fitting 66 can be designed in any suitable way for the inlet port 70 to be connectible with a source of irrigation fluid. The fitting 66 is shown by way of example as having a barb configuration for insertion in an end of irrigation fluid supply tubing. The irrigation passage 68 may be of uniform diameter from the inlet port 70 to the exit opening 72 as depicted for irrigation passage 68. The irrigation extension 64 may be disposed at an angle with the central longitudinal axis 59 of chamber 56, and the irrigation passage 68 may be disposed at the same angle to the central longitudinal axis 59 as the irrigation extension 64. The housing 46 is preferably formed by molding a suitable material such as plastic. The locking formation 48 and the irrigation extension 64 are preferably molded integrally and unitarily with the housing 46. The forward end of the irrigation extension 64 may be formed contiguous with or as a continuation of the profile of neck 49. The housing 46 may be of solid wall or solid material construction about or surrounding the chamber 56 and the irrigation passage 68.

Figure 8:
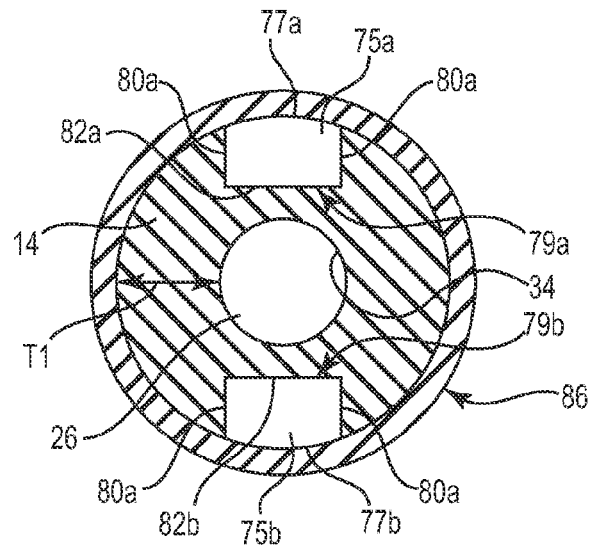
FIG. 8 is a cross-sectional view of a tubular outer member of the powered surgical tissue cutting instrument taken along line A-A of FIG. 1 and showing an irrigation passage of the irrigation system of the instrument.

A second irrigation passage 74a and a third irrigation passage 74b are disposed in the outer member 14 and form a further part of the irrigation system 12. The second irrigation passage 74a comprises a groove or trough 75a in or along the external or outer diameter surface of the main body length section 28 and extending longitudinally from an entry or inlet opening 76a of the groove located on or along the abutment surface 32 in fluid communication with access opening 58 to an outlet or discharge opening 78a of the groove located at or near the distal end of the outer member 14. Likewise, the third irrigation passage 74b comprises a groove or trough 75b in or along the external or outer diameter surface of the main body length section 28 and extending longitudinally away from an entry or inlet opening 76b of the groove located on or along the abutment surface 32 in fluid communication with access opening 58 to an outlet or discharge opening 78b of the groove located at or near the distal end of the outer member 14. FIG. 6 provides a close-up view of the discharge openings 78a and b. With further reference to FIG. 8, the grooves 75a and b are situated in their entirety within the wall thickness T1 of the main body length section 28 of the outer member 14 while being disposed external of the internal passage 26 in the outer member 14. The grooves 75a and b have open sides 77a and b, respectively, along the external surface of the main body length section 28, and have closed sides 79a and b, respectively, within the wall thickness T1 of the main body length section 28. The open sides 77a and b of the grooves 75a and b extend longitudinally from the entry openings 76a and b to the outlet openings 78a and b. The grooves 75a and b can have any suitable configuration in cross-section, and the cross-section of the grooves 75a and b can be uniform from the entry openings 76a and b to the outlet openings 78a and b. The entry openings 76a and b are defined by the edge of the closed sides 79a and b of the grooves 75a and b that are disposed along and in the plane of the abutment surface 32. The grooves 75a and b can be formed by cutting into the wall thickness T1 of the main body length section 28 of the outer member 14.

Figure 7:
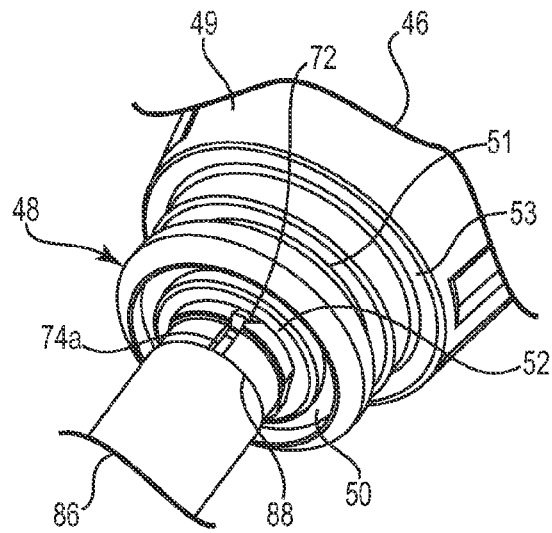
FIG. 7 is a perspective view of the powered surgical cutting instrument showing connection of an exit opening of a first irrigation passage with a second irrigation passage.

The grooves 75a and b is an example of one in which the closed sides 79a and b of the groove comprises and is defined by a pair of planar and parallel side walls or surfaces 80a and b of the groove extending inwardly from the external surface of the main body length section 28 to a planar bottom wall or surface 82a and b of the grooves. The bottom walls 82a and b extend between and connect the side walls 80a and b, and the bottom walls 82a and b are perpendicular to the side walls 80a and b. The side walls 80a and b and bottom walls 82a and b are disposed entirely within the wall thickness T1 and the grooves 75a and b are separated from the internal passage 26 by material that forms the wall of the main body length section 28. The grooves 75a and b extend longitudinally in parallel with the section of the central longitudinal axis 19 that extends along the main body length section 28. The groove 75a is located on the main body length section 28 so that the entry opening 76a on the abutment surface 32 is in alignment with the exit opening 72 on the front end surface 52 when the outer member 14 is mounted to the handpiece 18 with the main body length section 28 extending from the handpiece in the desired orientation. FIG. 7 shows alignment of irrigation passage 74a with exit opening 72. Accordingly, in the case of outer member 14, the groove 75a is located along the top of the main body length section 28. Due to the bevel surface of the access opening 58, inlet opening 76b of groove 75b is in fluid communication with the exit opening 72 such that fluid can be transferred from the first irrigation passage 68 to the third irrigation passage 74b.

As shown in FIGS. 4 and 7, the proximal length section 30 of the outer member 14 is secured within the chamber 56 of the handpiece 18 as described above so that the entry opening 76a of the groove 75a that forms the irrigation passage 74a in the outer member is aligned with the exit opening 72 of the irrigation passage 68 in the handpiece 18. Alignment of the handpiece irrigation passage 68 and the outer member irrigation passage 74a forms an irrigation channel 84a for the flow of irrigation fluid extending from the inlet port 70 of the fitting 66 at the rearward end of the irrigation extension 64 to the outlet opening 78a of the groove 75a at or near the distal end of the outer member 14. The irrigation channel 84a is thusly formed in part by the first irrigation passage 68 in the handpiece 18 and in part by the second irrigation passage 74a in the outer member 14. Access opening 58, being in fluid communication with the irrigation passage 68 and the irrigation passage 74b, forms a second irrigation channel 84b for the flow of irrigation fluid extending from the inlet port 70 of the fitting 66 to the outlet opening 78b of the groove 75b at or near the distal end of the outer member 14. The second irrigation channel 84b is thusly formed in part by the first irrigation passage 68 in the handpiece 18 and in part by the second irrigation passage 74b in the outer member 14.

The irrigation system 12 for the instrument 10 comprises the irrigation channels 84a and b and a tubular sleeve or sheath 86 disposed over the main body length section 28 of the outer member 14 with a snug or tight fit, whereby the irrigation channel 84a and b are enclosed and sealed between the inlet port 70 of the first irrigation passage 68 and the outlet openings 78a and b of the irrigation passages 74a and b. The sleeve 86 comprises a length of heat shrinkable tubing, such as heat shrinkable thermoplastic tubing, having a rearward end 88 spaced apart from the front end surface 52 of housing 46 and a forward end 90 disposed over the main body length section 28 adjacent the outlet openings 78a and b of the grooves 75a and b. The sleeve 86 extends longitudinally from its rearward end 88 to its forward end 90. In an alternative embodiment, the rearward end 88 of the sleeve 86 is disposed over the locking formation 48 and extends a distance proximally of the shoulder surface 53 of the locking formation 48 to terminate along the neck 49, wherein the boot 57 is eliminated.

Prior to heat shrinking, the sleeve 86 has an inner diameter large enough in size for the sleeve to be installed over the main body length section 28, typically by inserting the distal end of the outer member 14 within the sleeve 86 and sliding the sleeve over the main body length section until the rearward end 88 of the sleeve is positioned appropriately over the outer member 14. The sleeve 86 is heat shrunk over the main body length section 28 of the outer member 14, which reduces the diametric size of the sleeve to establish the snug or tight fit for the sleeve 86 on the main body length section 28. In one embodiment, the sleeve 86 can be trimmed as desired after heat shrinking to outer member 14. The heat shrunk sleeve 86 snugly or tightly engages the external or outer diameter surface of the main body length section 28 of the outer member 14 to extend across the open sides 77a and b of the grooves 75a and b while maintaining or allowing communication through the outlet openings 78a and b of the grooves for discharge of irrigation fluid from the irrigation channels 84a and b. The boot 57 and heat shrunk sleeve 86 close the open sides of the groove 75a and b and seal the irrigation passages 74a and b between the handpiece 18 and the forward end 90 of the sleeve 86 adjacent the outlet openings 78a and b of the grooves. The entire irrigation channel 84 is thusly sealed and enclosed from the inlet port 70 of the first irrigation passage 68 to the outlet opening 78s of the second irrigation passage 74a and the entire second irrigation channel is thusly sealed and enclosed from the inlet port 70 of the first irrigation passage 68 to the outlet opening 78b of the third irrigation passage 74b.

By using thin walled tubing for the sleeve 86, the presence of the sleeve 86 over the main body length section 28 does not appreciably add to the outer diameter of the main body length section. The interference or press fit retention of the proximal length section 30 of the outer member 14 in the chamber 56 of the housing 46 also acts as a seal to prevent leakage of irrigation fluid, together with sealing member 33. Therefore, irrigation fluid supplied to the inlet port 70 will flow through the irrigation channels 84a and b and will exit the forward end 90 of the sleeve 86 for discharge from the outlet openings 78a and b of the grooves 75a and b at or near the distal end of the outer member 14. It should be appreciated that the location at which the irrigation fluid is discharged from the irrigation channels 84a and b may depend on the location of the forward end 90 of the sleeve 86 along the grooves 75a and b. Depending on where the forward end 90 of the sleeve 86 is located along the grooves 75a and b, the outlet openings 78a and b of the grooves 75a and b may be comprised of the open top side of the grooves 75a and b and/or an end openings of the grooves within the wall thickness of the main body length section 28 similar to the entry openings 76a and b. In one embodiment, as illustrated in FIG. 6, outlet openings 78a and 78b include angled surfaces 92a and 92b that deflect irrigation fluid outwardly at the distal end 22 of the outer member 14.

Figure 5:
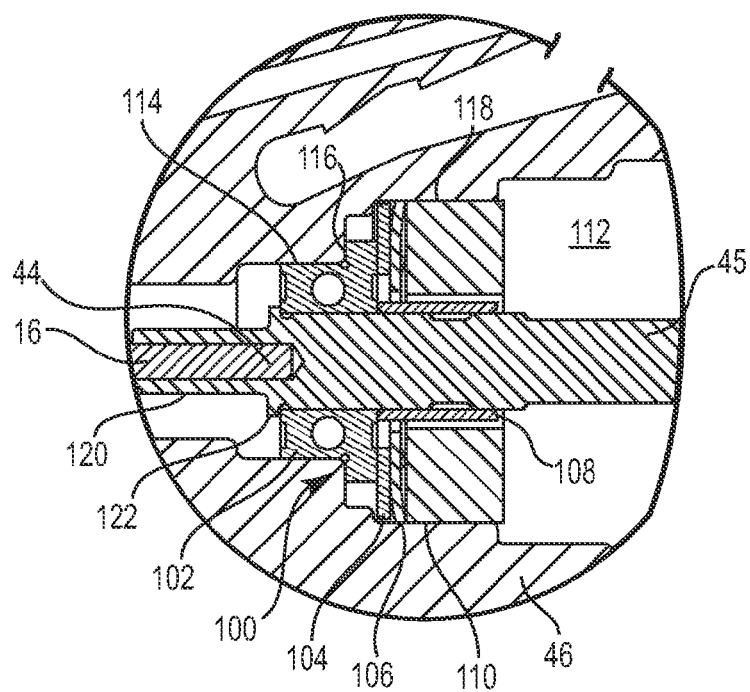
FIG. 5 is a close-up side view of the powered surgical cutting instrument in longitudinal cross-section showing connection of the handpiece with an inner member.

With reference to FIG. 5, a bearing assembly 100 allows inner member 16 and tang 45 to rotate relative to the housing 46. As illustrated, bearing assembly 100 includes a bearing 102, a rubber washer 104, a push-on ring 106, a spacer 108 and a felt washer 110. Bearing assembly 100 is positioned within a cavity 112 of the housing 46. In particular, bearing 102 is sized to fit within a first inner diameter 114 of cavity 112 and abut against an internal perpendicular surface 116 of cavity 112. Rubber washer 104 lies against a rear surface of the bearing 102 and is sized to fit within a second inner diameter 118 of cavity 112. Push-on ring 106 lies against rubber washer 104 and is configured to deflect so as to apply an axial load against inner diameter 118 of cavity 112 and secure bearing 102 and rubber washer 104 within the cavity 112. Spacer 108 is crimped to tang 45 and positioned so as to abut against a rearward surface of bearing 102. Felt washer 110 abuts against spring washer 106 and is configured to form an interference or press fit with the inner diameter 118 of cavity 112. During assembly, inner member 16 (i.e., at end 44) is welded to tang 45, for example with a bore 120 of the tang 145. Tang 45 also includes a tab 122 such that, upon insertion of the tang within the housing 46, tab 122 is positioned flush against a front surface of the bearing. As a result, tab 122 and spacer 108 are configured to axially secure the tang 45 with respect to the bearing 102.

To assemble instrument 10, cutting element 42 can be brazed to inner member 16. Outer member 14 can then be machined to form the grooves 75a and 75b therein. Sleeve 86 can then be heat shrunk over outer member 14 and trimmed to a length as desired. Bushing 91 can then be inserted within the distal opening 22 of the outer member 14, for example, with a press or interference fit. A lubricant can then be pumped into the passageway 26 of outer member 14. In one embodiment, the lubricant is a synthetic hydrocarbon material thickened with silica available, for example, from Nye Lubricants, Inc., of Fairhaven, Mass., under the trademark NYOGEL® 670. The inner member 16 can then be inserted within the outer member 14 and tang 45 can then be welded to inner member 16. Within the housing 46, the bearing, 102, rubber washer 104, and push-on ring 106 are inserted within the cavity 112. The assembled outer member 14, inner member 16, and tang 45 are then press fit within the housing 46. The spacer 108 can then be inserted over the tang 45 so as to be flush with a rearward surface of the bearing 102 such that the tang 45 is locked axially with respect to the bearing. Spacer 108 is then crimped to the tang 45. Felt washer 110 can then be inserted within the cavity 112. The boot 57 and ring 65 can be positioned over the sleeve 86 and ultimately boot 57 can be locked with respect to the locking formation 48 on housing 46. Once instrument 10 is assembled, the housing 46 can easily be coupled with an electric motor such that cutting element 42 is automatically locked and rotatable with operation of the motor. As a result, instrument 10 is a combination attachment and tool for coupling with a motor to perform a desired surgical procedure and does not require a surgeon or other end user to perform both an attachment step of the cutting element 42 to the handpiece 18 and coupling of the handpiece 18 to the motor 47.

The irrigation system 12 composed of the irrigation channels 84a and b and sleeve 86 is advantageous because it does not add appreciable bulk or volume to the outer member 14 and does not appreciably add to the external cross-sectional size of the outer member 14. Hence, the outer member 14 can be introduced in the patient's body through a smaller size anatomical portal than would be possible in an instrument having an external irrigation tube. Furthermore, the absence of an external irrigation tube along the outer member 14 provides greater room for endoscopic visualization within the patient's body and greater room for manipulation or maneuverability of the instrument within the patient's body compared to an outer member that has an external irrigation tube. The irrigation system 12 is virtually invisible to the surgeon and does not adversely affect visibility and access. Moreover, the irrigation system 12 maintains thermal performance of the instrument 10 at acceptable levels for patient contact by acting as a heat transfer medium.

Inasmuch as the present invention is subject to many variations, modifications and changes in detail, it is intended that all subject matter discussed above or shown in the accompanying drawings be interpreted as illustrative only and not be taken in a limiting sense.

Although the present disclosure has been described with reference to preferred embodiments, workers skilled in the art will recognize that changes can be made in form and detail without departing from the spirit and scope of the present disclosure.

What is claimed is:

1. A rotary powered surgical tissue cutting instrument comprising
an elongate tubular outer member including an open proximal end, a distal end, an internal passage, an opening in said distal end in communication with said internal passage, a main body length section having an external surface with an outer diameter, a proximal length section having an external surface with an outer diameter smaller than said outer diameter of said main body length section, an abutment surface between said external surface of said main body length section and said external surface of said proximal length section, said proximal length section extending proximally from said abutment surface to said proximal end of said outer member, said main body length section extending distally from said abutment surface to said distal end of said outer member;
an elongate inner member rotatably disposed within said internal passage of said outer member, said inner member including a proximal end, a distal end, a cutting element at said distal end of said inner member exposed from said opening in said outer member to cut anatomical tissue when said inner member is rotated within said outer member;
a powered surgical handpiece mounted to said proximal end of said outer member to maintain said outer member in a stationary position on said handpiece and mounted to said proximal end of said inner member to effectuate rotation of said inner member within said outer member, said handpiece including a housing having a front end with a front end surface and a chamber within said housing having an access opening on said front end surface, said proximal length section of said outer member extending through said access opening into said chamber of said housing with said abutment surface in abutment with said front end surface of said housing, said proximal end of said inner member extending proximally from said proximal end of said outer member to be rotatably driven within said handpiece; and
an irrigation system including a first irrigation passage in said handpiece having an inlet port connectible with a source of irrigation fluid and having an exit opening on said front end surface, a second irrigation passage in said outer member including a groove in said external surface of said main body length section extending longitudinally along said main body length section from an entry opening of said groove on said abutment surface to an outlet opening of said groove near said distal end of said outer member, said entry opening of said groove being aligned with said exit opening to form an irrigation channel for the flow of irrigation fluid extending from said inlet port of said first irrigation passage to said outlet opening of said second irrigation passage, and a sleeve disposed over said main body length section of said outer member, said sleeve extending longitudinally from a rearward end of said sleeve to a forward end of said sleeve disposed adjacent said outlet opening of said groove, said sleeve being disposed over said main body length section with a snug fit while allowing communication through said outlet opening of said groove for discharge of irrigation fluid from said irrigation channel, whereby said irrigation channel is enclosed and sealed between said inlet port of said first irrigation passage and said outlet opening of said second irrigation passage.

2. The rotary powered surgical tissue cutting instrument recited in claim 1 wherein said proximal length section of said outer member is sealingly retained in said chamber of said housing.

3. The rotary powered surgical tissue cutting instrument recited in claim 2 wherein said proximal length section is retained in said chamber with a press-fit.

4. The rotary powered surgical tissue cutting instrument recited in claim 1 wherein said sleeve is heat-shrunk over said main body length section of said outer member to establish said snug fit.

5. The rotary powered surgical tissue cutting instrument recited in claim 1 wherein said housing includes an irrigation extension extending from said front end to a fitting connectible with a source of irrigation fluid, said inlet port of said first irrigation passage is disposed in said fitting, and said first irrigation passage extends through said fitting, said irrigation extension, and said front end of said housing to said exit opening on said front end surface.

6. The rotary powered surgical tissue cutting instrument recited in claim 1 wherein said outer member includes a central longitudinal axis having a curved configuration between said handpiece and said distal end of said outer member, and said inner member conform to said curved configuration while being rotatable within said outer member.

7. The rotary powered surgical tissue cutting instrument recited in claim 6 wherein said cutting element comprises a bur.

8. A rotary powered surgical tissue cutting instrument comprising
an elongate tubular outer member including a central longitudinal axis, an open proximal end, a distal end, an internal passage, an opening in said distal end in communication with said internal passage, an inner diameter surface defining said internal passage, a main body length section having an external surface with an outer diameter and having a wall thickness between said external surface and said inner diameter surface, a proximal length section having an external surface with an outer diameter smaller than said outer diameter of said main body length section, said central longitudinal axis having a straight section along said proximal length section, said proximal length section being joined to said main body length section at an abutment surface, said external surface of said proximal length section extending proximally from said abutment surface to said proximal end of said outer member, said external surface of said main body length section extending distally from said abutment surface to said distal end of said outer member;
an elongate inner member rotatably disposed within said internal passage of said outer member, said inner member including a proximal end, a distal end, a cutting element at said distal end of said inner member exposed from said opening in said outer member to cut anatomical tissue when said inner member is rotated within said outer member;
a powered surgical handpiece mounted to said proximal end of said outer member to maintain said outer member in a stationary position on said handpiece and mounted to said proximal end of said inner member to effectuate rotation of said inner member, said handpiece including a housing having a front end comprising a neck and a locking formation extending from said neck to a front end surface of said housing, said housing including an inner diameter surface defining a chamber within said housing having an access opening on said front end surface, said chamber extending longitudinally proximally from said access opening through said locking formation and said neck, and an irrigation extension extending from said front end of said housing to terminate at an inlet port connectible with a source of irrigation fluid, said proximal length section of said outer member extending through said access opening and being received coaxially in said chamber with said abutment surface in abutment with said front end surface, said proximal end of said inner member extending proximally from said proximal end of said outer member to be rotatably driven within said handpiece; and
an irrigation system including a first irrigation passage in said handpiece, said first irrigation passage extending from said inlet port through said irrigation extension and said front end of said housing to an exit opening of said first irrigation passage along said front end surface, a second irrigation passage including a groove in said external surface of said main body length section of said outer member extending longitudinally along said main body length section from an entry opening of said groove on said abutment surface to an outlet opening of said groove near said distal end of said outer member, said groove having an open side along said external surface of said main body length section and said groove being disposed entirely within said wall thickness of said main body length section, said entry opening of said groove being aligned with said exit opening to form an irrigation channel for the flow of irrigation fluid extending from said inlet port of said first irrigation passage to said outlet opening of said groove, and a sleeve disposed over said main body length section of said outer member, said sleeve extending longitudinally from a rearward end of said sleeve to a forward end of said sleeve disposed adjacent said outlet opening of said groove, said sleeve being disposed over said main body length section with a snug fit while allowing communication through said outlet opening of said groove for discharge of irrigation fluid from said irrigation channel, said sleeve forming a seal with said locking formation and closing said open side of said groove, whereby said irrigation channel is enclosed and sealed between said inlet port of said first irrigation passage and said outlet opening of said second irrigation passage.

9. The rotary powered surgical tissue cutting instrument recited in claim 8 and further comprising a boot positioned over the locking formation and providing a seal between said rearward end of the sleeve and the first irrigation passage.

10. The rotary powered surgical tissue cutting instrument recited in claim 9 wherein a locking ring is disposed over the boot to secure the boot to said outer member.

11. The rotary powered surgical tissue cutting instrument recited in claim 10 wherein said sleeve comprises a length of thin-walled tubing heat-shrunk over said main body length section of said outer member.

12. The rotary powered surgical tissue cutting instrument recited in claim 8 wherein said chamber has a central longitudinal axis, said front end surface is planar and perpendicular to said central longitudinal axis of said chamber, and said abutment surface is planar and perpendicular to said straight section of said central longitudinal axis of said outer member.

13. The rotary powered surgical tissue cutting instrument recited in claim 12 wherein said irrigation extension extends proximately from said neck of said housing at an angle with said central longitudinal axis of said chamber.

14. The rotary powered surgical tissue cutting instrument recited in claim 8 wherein said external surface of said proximal length section of said outer member has an outer diameter of a size to be received within said chamber with a press-fit to establish a seal between said proximal length section and said inner diameter surface of said housing.

15. The rotary powered surgical tissue cutting instrument recited in claim 8 wherein said locking formation and said irrigation extension are molded integrally, unitarily with said housing.

16. The rotary powered surgical tissue cutting instrument recited in claim 8 wherein said groove includes a pair of planar parallel side walls extending from said external surface of said main body length section to a planar bottom wall of said groove, said bottom wall extending between said side walls within said wall thickness of said main body length section.

17. A rotary powered surgical tissue cutting instrument comprising
an elongate tubular outer member including a central longitudinal axis, an open proximal end, a distal end, an inner diameter surface defining an internal passage coaxial with said central longitudinal axis, an opening in said distal end in communication with said internal passage, a main body length section having an external surface with an outer diameter and having a wall thickness between said external surface and said inner diameter surface, a proximal length section having an external surface with an outer diameter smaller than said outer diameter of said main body length section, said central longitudinal axis having a straight section along said proximal length section, said proximal length section being joined to said main body length section at an annular abutment surface extending around said external surface of said proximal length section, said abutment surface being planar and perpendicular to said straight section of said central longitudinal axis, said proximal length section extending proximally from said abutment surface to said proximal end of said outer member, said main body length section extending distally from said abutment surface to said distal end of said outer member;
an elongate inner member rotatably disposed within said internal passage of said outer member, said inner member including a proximal end, a distal end, a cutting element at said distal end of said inner member exposed from said opening in said outer member to cut anatomical tissue when said inner member is rotated within said outer member;
a powered surgical handpiece mounted to said proximal end of said outer member to maintain said outer member in a stationary position on said handpiece and mounted to said proximal end of said inner member to effectuate rotation of said inner member within said outer member, said handpiece including a housing having a front end comprising a neck and a locking formation joined to said neck, and a planar front end surface, said housing further including an inner diameter surface defining a chamber within said housing having a chamber within said housing having an access opening on said front end surface, and having a straight central longitudinal axis perpendicular to said shoulder surface said front end surface, said proximal length section of said outer member extending through said access opening and being received coaxially in said chamber of said housing with said abutment surface in abutment with said front end surface of said housing, said proximal length section being sealingly secured in said chamber by engagement of said external surface of said proximal length section with said inner diameter surface of said housing, said proximal end of said inner member extending proximally from said proximal end of said outer member to be rotatably driven within said handpiece; and
an irrigation system including a first irrigation passage in said handpiece extending from said inlet port through said irrigation extension, said neck and said locking formation to an exit opening of said first irrigation passage located on said front end surface, a second irrigation passage including a groove within said wall thickness of said main body length section having an entry opening on said abutment surface, an outlet opening near said distal end of said outer member and an open side along said external surface of said main body length section extending longitudinally from said entry opening to said outlet opening, said entry opening of said groove being aligned with said exit opening on said front end surface to form an irrigation channel for the flow of irrigation fluid extending from said inlet port of said first irrigation passage to said outlet opening of said second irrigation passage, and a sleeve disposed over said main body length section of said outer member, said sleeve extending longitudinally from a rearward end of said sleeve to a forward end of said sleeve disposed adjacent said outlet opening of said groove, said sleeve being disposed over said main body length section with a snug fit while allowing communication through said outlet opening of said groove for discharge of irrigation fluid from said irrigation channel, whereby said irrigation channel is enclosed and sealed between said inlet port of said first irrigation passage and said outlet opening of said second irrigation passage.

18. The rotary powered surgical tissue cutting instrument recited in claim 17 wherein said central longitudinal axis of said outer member is curved along said main body length section and said cutting element is a bur.

19. The rotary powered surgical tissue cutting instrument recited in claim 18 wherein said groove extends longitudinally in parallel with said central longitudinal axis of said outer member along said main body length section of said outer member.

20. The rotary powered surgical tissue cutting instrument recited in claim 17 wherein a locking recess receives tabs of a boot disposed over the locking formation.

21. The rotary powered surgical tissue cutting instrument recited in claim 17 wherein said outer member includes a second irrigation channel enclosed and sealed between said inlet port of said first irrigation passage and an outlet opening of a third irrigation passage.

* * * * *